United States Patent
Lee et al.

(10) Patent No.: US 8,048,387 B2
(45) Date of Patent: Nov. 1, 2011

(54) CENTRIFUGAL MICROFLUIDIC DEVICE HAVING SAMPLE DISTRIBUTION STRUCTURE AND CENTRIFUGAL MICROFLUIDIC SYSTEM INCLUDING THE CENTRIFUGAL MICROFLUIDIC DEVICE

(75) Inventors: Beom-seok Lee, Hwaseong-si (KR); Yoon-kyoung Cho, Suwon-si (KR); Jong-myeon Park, Seoul (KR); Jung-nam Lee, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 158 days.

(21) Appl. No.: 12/108,823

(22) Filed: Apr. 24, 2008

(65) Prior Publication Data
US 2008/0269077 A1    Oct. 30, 2008

(30) Foreign Application Priority Data
Apr. 24, 2007  (KR) .................. 10-2007-0040039

(51) Int. Cl.
*G01N 35/00* (2006.01)
(52) U.S. Cl. .......... 422/506; 422/507; 422/502; 422/72; 422/504; 422/64; 436/45; 436/165; 436/177; 436/180
(58) Field of Classification Search ............... 422/68.1, 422/72, 502–507, 537; 435/287.9; 494/16, 494/17, 23, 27, 29, 31–34; 436/180, 179; 366/220; 137/803, 814; 210/512.1
See application file for complete search history.

(56) References Cited

U.S. PATENT DOCUMENTS

| | | | |
|---|---|---|---|
| 5,693,233 A | 12/1997 | Schembri | |
| 6,235,531 B1 * | 5/2001 | Kopf-Sill et al. | 422/72 |
| 6,319,469 B1 | 11/2001 | Mian et al. | |
| 6,527,432 B2 * | 3/2003 | Kellogg et al. | 422/72 |
| 6,548,788 B2 * | 4/2003 | Kellogg et al. | 219/543 |
| 6,637,463 B1 * | 10/2003 | Lei et al. | 137/803 |
| 2003/0156991 A1 * | 8/2003 | Halas et al. | 422/100 |
| 2004/0120856 A1 * | 6/2004 | Andersson et al. | 422/72 |
| 2008/0101993 A1 * | 5/2008 | Andersson et al. | 422/72 |

FOREIGN PATENT DOCUMENTS

| | | |
|---|---|---|
| EP | 0325690 A1 | 1/1990 |
| FR | 2575293 A1 | 6/1986 |
| WO | 93/16391 A1 | 8/1993 |
| WO | 95/06870 A1 | 3/1995 |
| WO | 95/33986 A1 | 12/1995 |

* cited by examiner

*Primary Examiner* — In Suk Bullock
*Assistant Examiner* — Sharon Pregler
(74) *Attorney, Agent, or Firm* — Sughrue Mion, PLLC

(57) ABSTRACT

Provided are a centrifugal microfluidic device having a sample distribution structure and a centrifugal microfluidic system including the centrifugal microfluidic device. The centrifugal microfluidic device includes: a rotatable platform; a sample chamber which is disposed in the rotatable platform and houses a fluid sample; a distribution channel connected to an outlet of the sample chamber; a valve which is disposed in the outlet of the sample chamber; a plurality of non-vented reaction chambers which are disposed in the rotatable platform outside of the distribution channel in the radial direction; and a plurality of inlet channels connecting the distribution channel with the reaction chambers.

29 Claims, 7 Drawing Sheets

CENTRIFUGAL MICROFLUIDIC DEVICE HAVING SAMPLE DISTRIBUTION STRUCTURE AND CENTRIFUGAL MICROFLUIDIC SYSTEM INCLUDING THE CENTRIFUGAL MICROFLUIDIC DEVICE

CROSS-REFERENCE TO RELATED PATENT APPLICATION

This application claims priority from Korean Patent Application No. 10-2007-0040039, filed on Apr. 24, 2007 in the Korean Intellectual Property Office, the disclosure of which is incorporated herein in its entirety by reference.

BACKGROUND OF THE INVENTION

1. Field of the Invention

The present invention relates to a centrifugal microfluidic device and a centrifugal microfluidic system including the centrifugal microfluidic device, and more particularly, to a centrifugal microfluidic device that can distribute a sample to a plurality of non-vented chambers using one moving operation of the sample, and a centrifugal microfluidic system including the centrifugal microfluidic device.

2. Description of the Related Art

Generally, a microfluidic device has a structure including a chamber storing a minute amount of fluid, a channel through which the fluid flows, a valve for controlling the fluid flow, and various functional units receiving the fluid to perform predetermined operations. The functional units also have a basic structure including a chamber, a channel, or a valve, and can be configured in different combinations. A biochip is obtained by arranging such microfluidic device on a chip-type substrate and is used to analyze the performance of various assays including biologic reactions. In particular, a device that is designed to perform multiple step processes and manipulations using a single chip is referred to as a lab-on-a chip.

A driving pressure is generally required to transfer a fluid within a microfluidic device. A capillary pressure or a pressure generated by a specifically designed pump is used as the driving pressure. A lab compact disk (CD) or a lab-on a disk, based on the use of centrifugal force, has been recently developed as a microfluidic device by arranging microfluidic structures on a compact disk-shaped platform. However, in this case, a microfluidic structure is not fixed to a rotating frame, compared to the case of a lab-on-a chip where microfluidic structure is fixed to a bottom part. Additionally, fluid pumping using the centrifugal force is easy, however, an operation for controlling the fluid (e.g., individual driving of a valve or distribution of the fluid) is difficult.

In biochemical, biological, or medical applications where microfluidic devices are mainly used, it is necessary to distribute a sample (fluid) to a plurality of reaction chambers in order to simultaneously examine the reaction of the sample with respect to various reaction liquids. Such centrifugal microfluidic devices have been disclosed in U.S. Pat. Nos. 5,591,643 and 5,518,930. However, there is still a need for a microfluidic device having a structure in which a sample can be effectively distributed as soon as possible without waiting for a movement of a fluid sample due to a capillary phenomenon or adding a resistance to the movement of the fluid.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above.

The present invention provides a centrifugal microfluidic device that can distribute a sample to a plurality of reaction chambers having no vent using one sample moving operation (rotation of the microfluidic device), and a centrifugal microfluidic system including the centrifugal microfluidic device. The centrifugal microfluidic device of the present invention has a simple construction of a microfluidic structure and removes a resistance factor, so that a sample can be rapidly distributed.

According to an aspect of the present invention, there is provided a centrifugal microfluidic device including a rotatable platform; a sample chamber disposed in the platform and housing a fluid sample; a distribution channel connected to an outlet of the sample chamber; a valve which is disposed in the outlet of the sample chamber; a plurality of non-vented reaction chambers disposed outside of a radial direction of the distribution channel in the platform; a plurality of inlet channels respectively connecting the distribution channel with the reaction chambers; and a sample distribution structure in which the fluid sample housed in the sample chamber is distributed to the plurality of non-vented reaction chambers through the distribution channel by a centrifugal force due to a rotation of the platform.

Each of the inlet channels may further include a barrier rib branching an inner part of the inlet channel into two sub channels. In this case, the inside of the barrier rib may clog a part of the distribution channel, and thus a fluid resistance generated when the fluid sample proceeds along the distribution channel may be less than or equal to a fluid resistance generated when the fluid sample proceeds towards the sub channel.

According to an aspect of the present invention, the centrifugal microfluidic device may further include a guide protrusion that guides a fluid sample flowing along the distribution channel and is formed at a portion where the inlet channel is connected to the distribution channel. The guide protrusion may protrude towards the inlet channel at an intersection between an inner wall of the distribution and a central line that extends to equally divide a width of the inlet channel.

According to an aspect of the present invention, a fluid resistance at inlet channels may be greater than a fluid resistance at the distribution channel. The distribution channel may include a consecutive wave section and connects the non-vented reaction chamber to the consecutive wave section so that a distance between the non-vented reaction chamber to the consecutive wave section is minimized.

According to another aspect of the present invention, there is provided a centrifugal microfluidic system including: one of the above centrifugal microfluidic devices; a rotation driving unit rotating so as to support the centrifugal microfluidic device and control the centrifugal microfluidic device; and a valve driving unit individually driving a valve selected in the centrifugal microfluidic device.

The valve driving unit may include: an external energy source emitting an electromagnetic wave that can help a heating particle in the valve to heat; and an external energy source controller controlling a location and a direction of the external energy source so that the electromagnetic wave emitted by the external energy source is intensively incident on a region corresponding to the selected valve. The external energy source controller may include a straight moving unit such that the external energy source facing a platform of the microfluidic device is moved in a radial direction of the platform. The external energy source supplier may include a plane moving unit moving the external energy source facing the platform of the microfluidic device in two directions on a plane parallel to the platform with respect to rectangular coordinates.

In addition, the centrifugal microfluidic system may further include a light detector that can optically detect a reaction result of each of the reaction chambers of the centrifugal microfluidic device.

BRIEF DESCRIPTION OF THE DRAWINGS

The above and other aspects of the present invention will become more apparent by describing in detail exemplary embodiments thereof with reference to the attached drawings in which.

DETAILED DESCRIPTION OF EXEMPLARY EMBODIMENTS OF THE INVENTION

Figure 1:
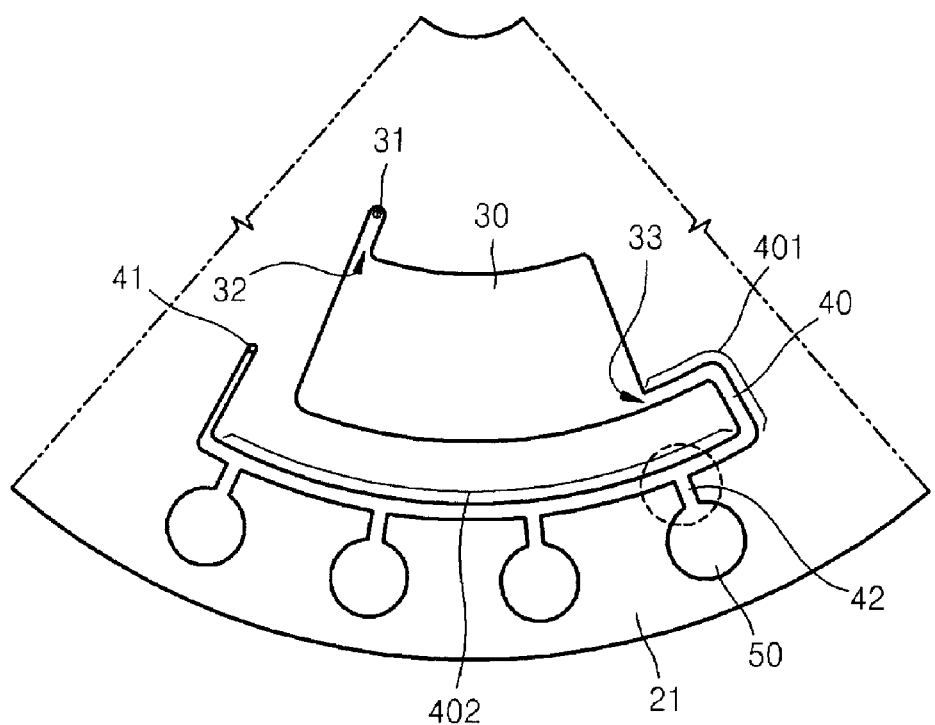
FIG. 1 is a plan view of a centrifugal microfluidic device according to an exemplary embodiment of the present invention.

Hereinafter, the present invention will be described in detail by explaining exemplary embodiments of the invention with reference to the attached drawings. Like reference numerals in the drawings denote like elements. In the drawings, the shapes of illustrated chambers, channels, or the like are simplified, and the sizes of the chambers, channels, or the like are exaggerated for clarity. A sample denotes a material in which a fluid having a living sample (e.g., blood, saliva, or urine) is mixed with a particle having a greater intensity than that of the fluid. In addition, the inside and outside of a platform respectively denote a part that is relatively close to a center of rotation of the platform and a part that is relatively far from the center of rotation of the platform.

FIG. 1 is a plan view of a centrifugal microfluidic device according to an exemplary embodiment of the present invention. The centrifugal microfluidic device includes a disc-type platform 21 comprising structures 30, 40, 42, and 50 that provide spaces housing a fluid in the platform 21 and flow paths along which a fluid flows. However, the platform 21 is not limited to a disk type and may be a structure that can be rotated or mounted to a rotatable frame, wherein the width of the structure may be relatively greater than the thickness of the structure. Hereinafter, the platform 21 will be described to have a disk type.

The platform 21 may be formed of a plastic material, e.g., acryl and polydimethylsiloxane (PDMS), that can be easily molded and whose surface is biologically non-active, but is not limited thereto. That is, the platform 21 may be formed of a material having chemical and biological stability, optical transparency, and mechanical workability. The platform 21 may include various plates. An engraved structure corresponding to a chamber or a channel may be formed on an interface between the plates and the plates are bonded to each other. Thus, a space and a path can be provided in the platform 21 (see FIG. 6). The plates may be bonded to each other using various methods such as adhesion in which adhesives or double-sided adhesive tapes are used, ultrasonic fusion, and laser welding.

The microfluidic device includes a sample chamber 30 housing a fluid sample. An inlet 32 of the sample chamber 30 may be connected to an injection inlet 31 to which a sample is injected from the outside. The inlet 32 may be connected to other structures (not shown) in the platform 21, and may receive a sample from the other structures. An outlet 33 of the sample chamber 30 may be disposed on the farthest part of the sample chamber 30 from the center of rotation of the platform 21 because a sample housed inside the outlet 33 is discharged when the fluid sample is moved by the centrifugal force. However, the present invention is not limited thereto. For example, an outlet may be formed on various parts of the sample chamber 30.

A distribution channel 40 is connected to the outlet 33 of the sample chamber 30. The distribution channel 40 includes a first section 401, which extends from the outlet 33 towards the outside of the platform 21, and a second section 402, which extends from an outer end of the first section 401 along a circumference of the microfluidic device. An end of the second section 402 may be connected to an vent 41. The vent 41 may be disposed on a portion so that a sample may not leak when a sample is moved from the sample chamber 30 to the distribution channel 40 by centrifugal force. The distribution channel 40 is formed so that the fluid resistance may be unchanged from a front end connected to the outlet 33 of the sample chamber 30 to a rear end connected to the vent 41, that is, throughout the entire sections including the first section 401 and the second section 402. The cross section of the distribution channel 40 may be the same throughout the entire sections so that the fluid resistance may be unchanged. Accordingly, the resistance against the movement of a fluid is minimized, which can be easily generated during a sample distribution, and thus the sample can be easily and rapidly distributed.

A plurality of non-vented reaction chambers 50 are disposed outside of the distribution channel 40 formed in the platform 21. The non-vented reaction chambers 50 have no vent for exhaustion discharge. Various kinds and various concentrations of reagents may be beforehand injected into the reaction chambers 50, and the reagents can react with the fluid sample distributed through the distribution channel 40, and this reaction can be optically detected. For example, the reaction, which can be optically detected, may be a fluorescent expression or change of optical density. However, the use of the reaction chamber 50 is not limited thereto.

The non-vented reaction chambers 50 are connected to the second section 402 of the distribution channel 40 through respective inlet channels 42. The inlet channels 42 are respectively connected to the distribution channel 40 in a "T" shape as indicated by a region defined by dotted lines illustrated in FIG. 1. At this time, the inlet channels 42 may be arranged in a direction of a radius of gyration of the platform 21.

Figure 2:
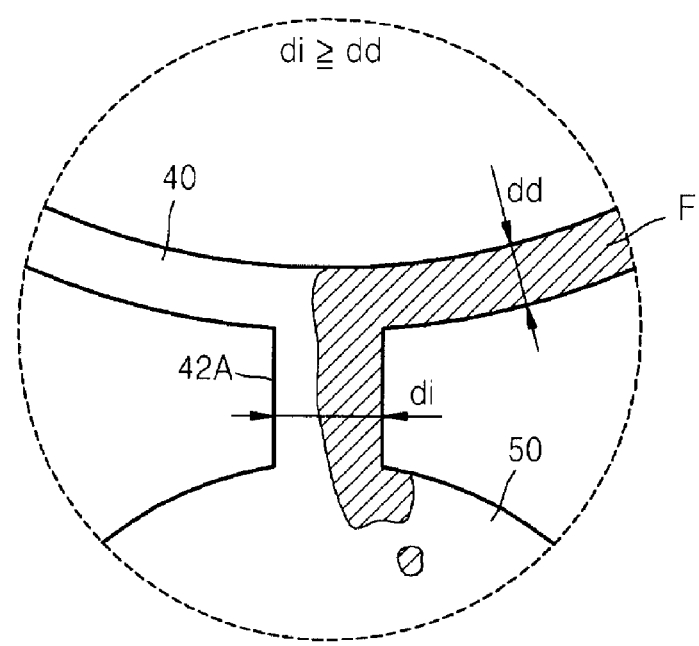
FIG. 2 is an enlarged plan view of the region defined by in FIG. 1, according to an exemplary embodiment of the present invention.

FIG. 2 is an enlarged plan view of the region defined by dotted lines in FIG. 1, according to an exemplary embodiment of the present invention. Referring to FIG. 2, an inlet channel 42A of a single channel type is illustrated as an example of the inlet channel 42 illustrated in FIG. 1. Most of the fluid sample, which is provided from the reaction chamber 50 to the distribution channel 40 by the centrifugal force, proceeds towards the reaction chamber 50 along the inlet channel 42A from the distribution channel 40 because a direction of the centrifugal force applied to the fluid sample coincides with a flow direction in the inlet channel 42A. The cross section of the inlet channel 42A may be greater than or equal to that of the distribution channel 40 so that a sample F may not occupy the entire inlet channel 42A, and air from the reaction chamber 50 may go out through the inlet channel 42A when the sample F provided through the distribution channel 40 flows into the reaction chamber 50. When the depth of the distribution channel 40 is the same as that of the inlet channel 42A, the width 'dd' of the distribution channel 40 and the width 'di' of the inlet channel 42A may satisfy the inequality di≧dd. However, the inequality di≧dd is not always satisfied because although the inlet channel 42A is clogged by the sample F when an empty space exists in the reaction chamber 50, if the cross section of the inlet channel 42A is large enough, the centrifugal force applied to the sample F of the inlet channel 42A becomes greater than a surface tension of the sample F. Thus, while the surface tension of the sample F is vanishing, the sample F is moving into the reaction chamber 50 in the form of droplets, and air bubbles having a volume corresponding to the moved sample F can move into distribution channel 40.

When the reaction chamber 50 is filled with the sample F by the above process, the sample F stops flowing into the reaction chamber 50, and the sample F moves along the distribution channel 40 to fill a next reaction chamber (not shown). However, when the reaction chamber 50 is not filled with the sample F, a part of the sample F can proceed towards the next reaction chamber.

Figure 3:
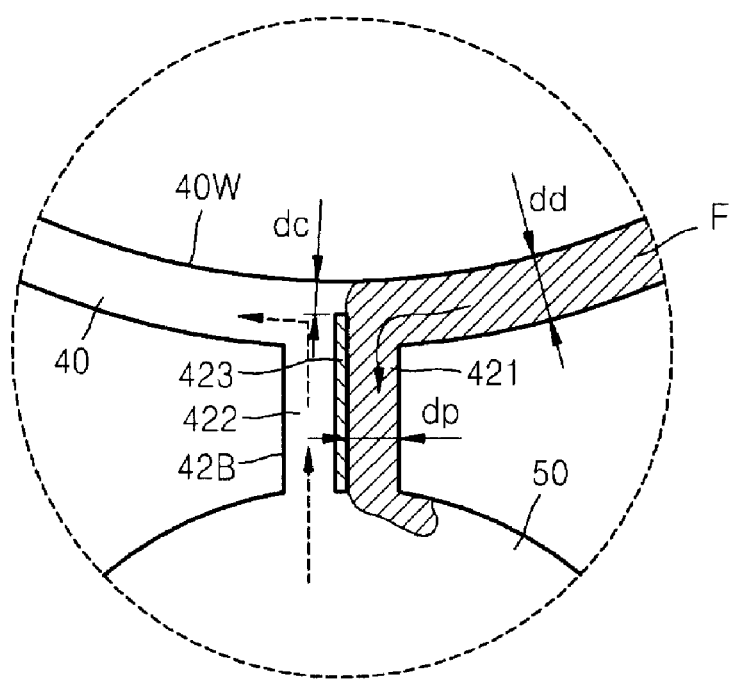
FIG. 3 is an enlarged plan view of the region defined by dotted lines in FIG. 1, according to another exemplary embodiment of the present invention.

FIG. 3 is an enlarged plan view of the region defined by the dotted lines in FIG. 1, according to another exemplary embodiment of the present invention. Referring to FIG. 3, an inlet channel 42B of a multi channel type is illustrated as another example of the inlet channel 42 illustrated in FIG. 1. The inlet channel 42B of the multi channel type includes a barrier rib 423 that is disposed in the middle of the inlet channel 42B in a direction parallel to the inlet channel 42B. The barrier rib 423 may be disposed so that an inner end of the barrier rib 423 may partially clog a flow path towards the distribution channel 40. The inlet channel 42B is branched into two sub channels 421 and 422 by the barrier rib 423. The barrier rib 423 guides a sample F flowing along the distribution channel 40 that may preferentially flow into the reaction chamber 50 along the sub channel 421 of the front (based on a proceeding direction of the sample F) of the barrier rib 423.

At this time, air is discharged towards the distribution channel 40 through the sub channel 422, wherein the quantity of the air corresponds to the volume of the sample F flowing into the reaction chamber 50. When the reaction chamber 50 is filled the sample F through this process, the sample F stops flowing into the inlet channel 42B, and the sample F starts proceeding between an inner end of the barrier rib 423 and an inner wall 40W of the distribution channel 40 along the distribution channel 40.

The inside (based on a radius of gyration) of the barrier rib 423 clogs a part of the distribution channel 40, and thus a resistance generated when the sample F proceeds along the distribution channel 40 may be less than or equal to a resistance generated when the sample flows towards the sub channel 421. For example, the cross section of a part, through which a fluid can flow between an inner end of the barrier rib 423 and the inner wall 40W of the distribution channel 40, may be less than or equal to the cross section of each of the sub channels 421 and 422. In particular, when the depth of the distribution channel 40 is the same as that of the inlet channel 42B, 'dc' and 'dp', which are indicated in FIG. 3, satisfy the inequality dc≦dp.

Figure 11:
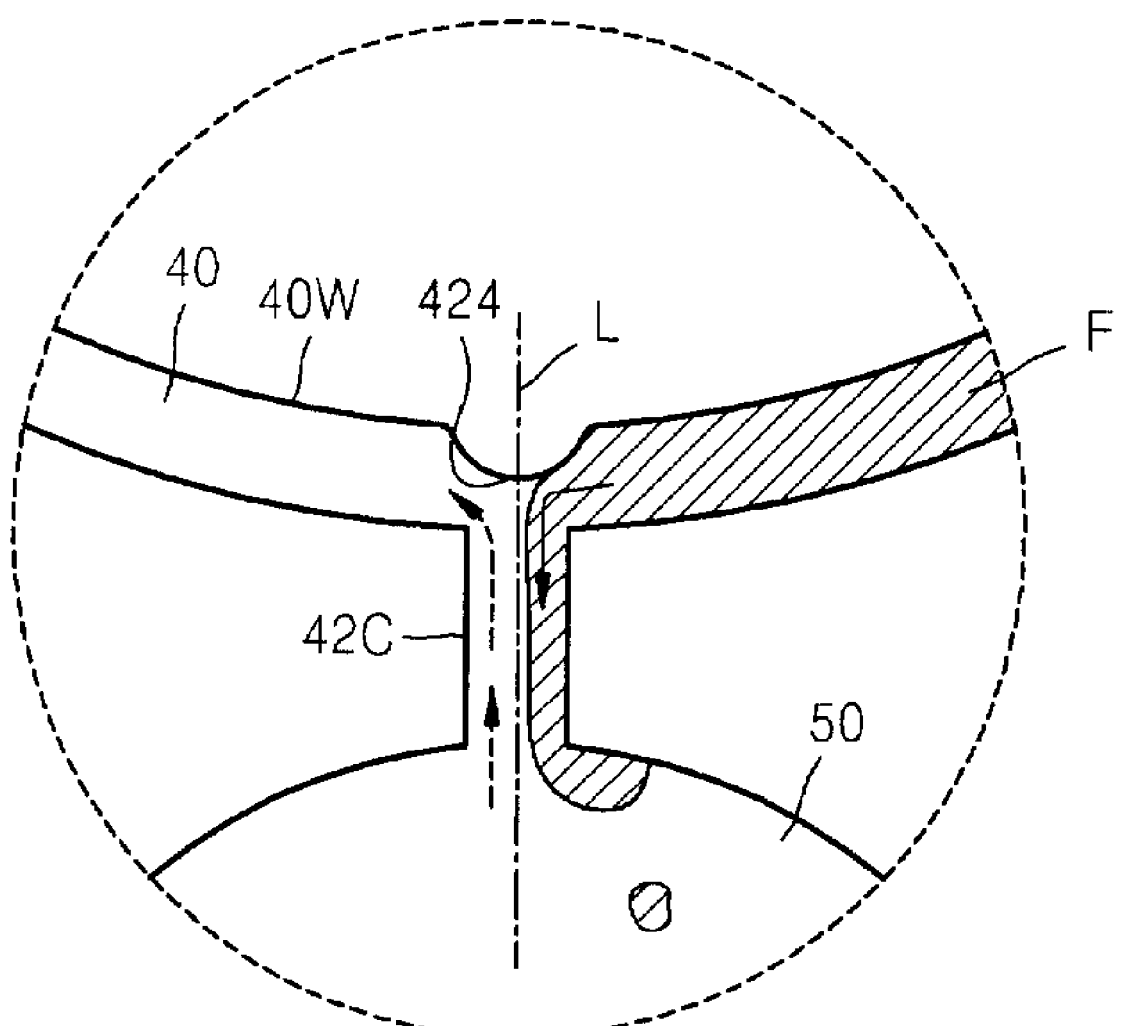
FIG. 11 is an enlarged plan view of the region defined by dotted lines in FIG. 1, according to another exemplary embodiment of the present invention.

FIG. 11 is an enlarged plan view of the region defined by dotted lines in FIG. 1, according to another exemplary embodiment of the present invention. Referring to FIG. 11, a distribution channel 40 includes a guide protrusion 424 that guides a fluid sample F flowing along the distribution channel 40 to an inlet channel 42C. The guide protrusion 424 is formed at a portion where the inlet channel 42C is connected to the distribution channel 40. In particular, the guide protrusion 424 protrudes towards the inlet channel 42C at an intersection between an inner wall 40W of the distribution channel 40 and a central line L that extends to equally divide the width of the inlet channel 42C. When the sample F flowing along the distribution channel 40 flows into the inlet channel 42C by a centrifugal force due to a rotation of a platform 21, the sample F is further deflected in a radial direction of the platform 21 by the guide protrusion 424. Accordingly, a portion of a cross section of the inlet channel 42C may not be clogged. As such, the air in a reaction chamber 50 may be exhausted via a part of the inlet channel 42C that is opened.

Figure 4:
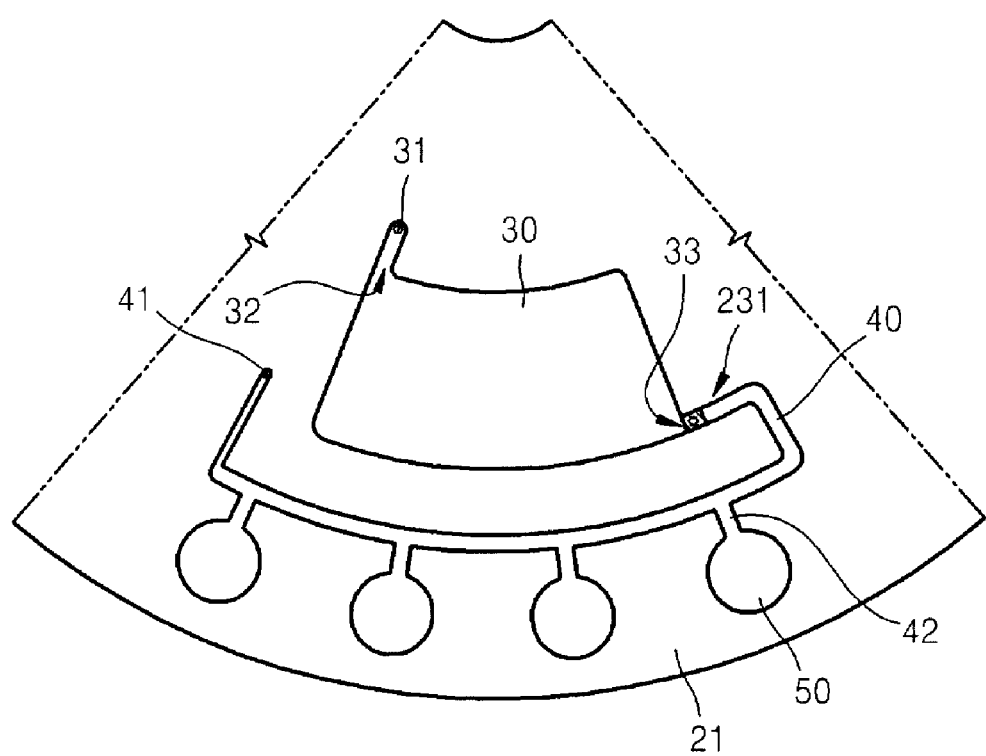
FIG. 4 is a plan view of a centrifugal microfluidic device according to another exemplary embodiment of the present invention.

FIG. 4 is a plan view of a centrifugal microfluidic device according to another exemplary embodiment of the present invention. The microfluidic device of FIG. 4 is similar to the microfluidic device of FIG. 1 except that the microfluidic device of FIG. 4 further includes a phase transition type normally closed valve 231 on an outlet 33 of a sample chamber 30. According to the current exemplary embodiment of the present invention, the inlet channel 42 may be the inlet channel 42A of the single channel type illustrated in FIG. 2 or the inlet channel 42B of the multi channel type illustrated in FIG. 3.

Figure 12:
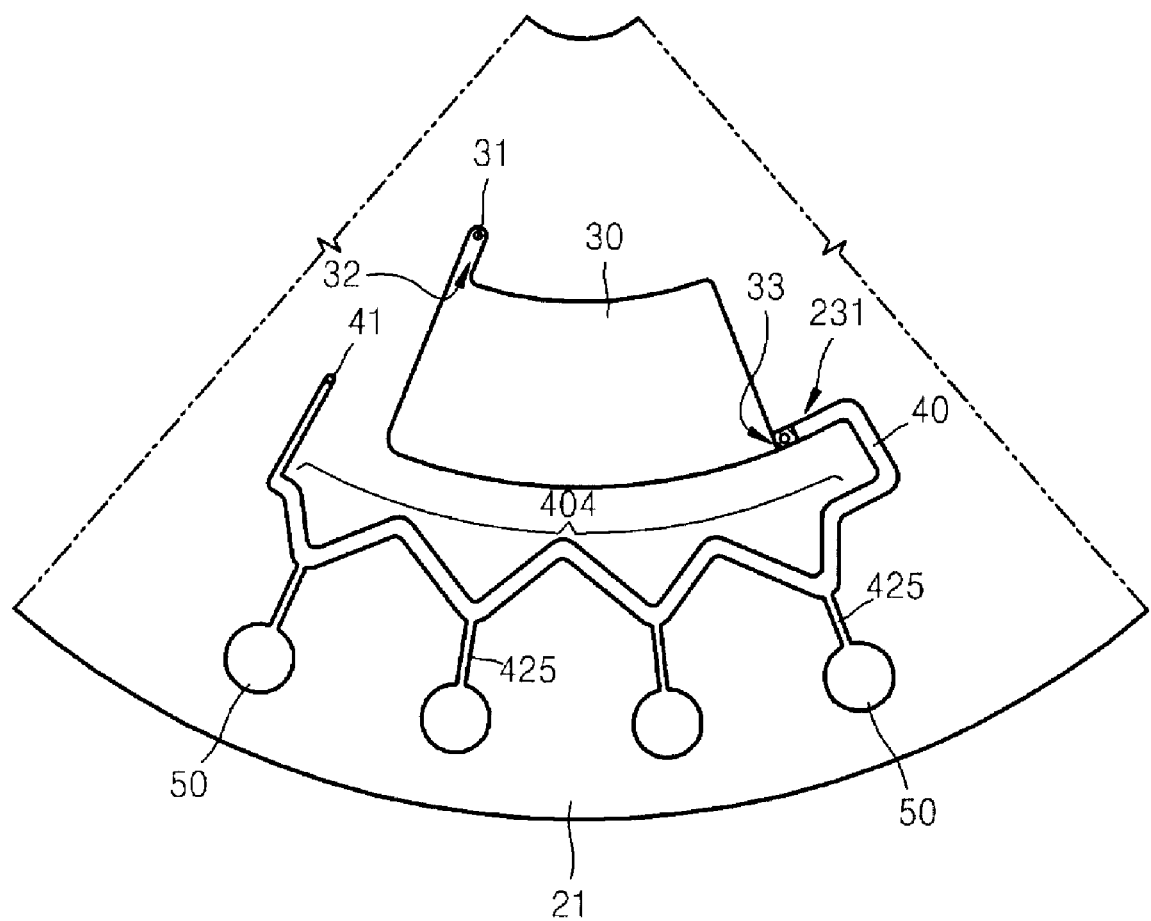
FIG. 12 is a plan view of a centrifugal microfluidic device according to another exemplary embodiment of the present invention.

FIG. 12 is a plan view of a centrifugal microfluidic device according to another exemplary embodiment of the present invention. The centrifugal microfluidic device includes a phase transition type normally closed valve 231 formed at an outlet 33 of a sample chamber 30. A distribution channel 40 connected to the sample chamber 30 includes a consecutive wave section 404 having triangular wave shape structure. A plurality of reaction chambers 50 are connected to the consecutive wave section 404 by respective inlet channels 425. The inlet channels 425 are configured so that a distance between the reaction chambers 50 and the consecutive wave section 404 is minimized. The fluid resistance at each inlet channel 425 may be greater than the fluid resistance at the distribution channel 40. To achieve this, the width of the inlet channels 425 may be smaller than the width of the distribution channel 40.

In the centrifugal microfluidic device of FIG. 12, a sample housed in the sample chamber 30 may be distributed to the reaction chamber 50 by a two-step rotation of the platform 21. That is, after the phase transition type normally closed valve 231 is opened, the sample may be moved into the consecutive wave section 404 by a first step of the rotation of the platform 21. Then, the sample may be injected into the reaction chambers 50 via the inlet channels 425 by a second step in which the platform 21 is rotated at higher speed than that of the first step. The centrifugal microfluidic device can meter the sample by the first step of the rotation of the platform 21, and thus another unit for metering the sample is not required. Although not illustrated, the centrifugal microfluidic device may further include a unit that performs an additional process using the sample and is disposed at the inlet channel 425.

Referring to FIG. 4, the phase transition type normally closed valve 231 is a valve that contactlessly receives an energy from an external energy source disposed outside of the microfluidic device to be driven, and is of a normally closed (NC) type. A detailed construction of the phase transition type normally closed valve 231 is as follows.

Figure 5:
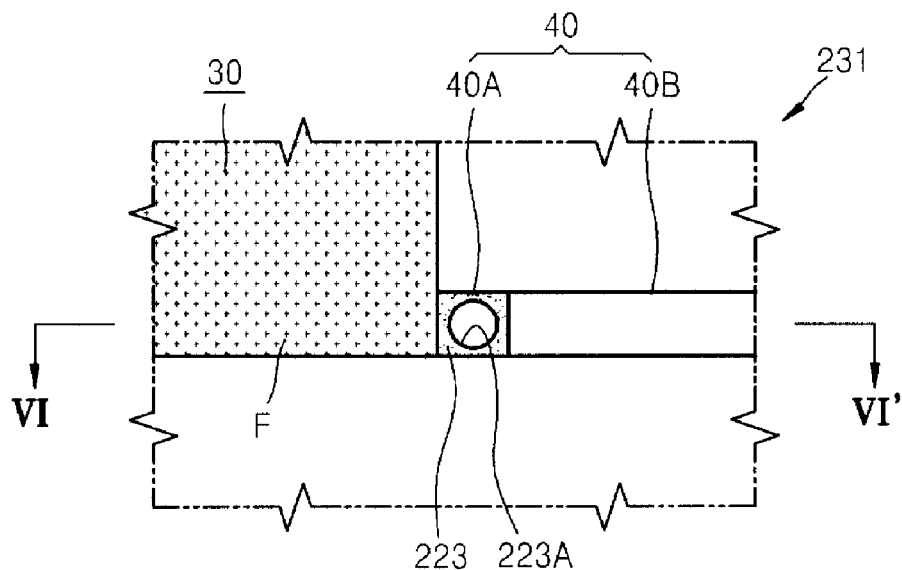
FIG. 5 is a plan view of the phase transition type normally closed valve that is used in the microfluidic device of FIG. 4.
Figure 6:
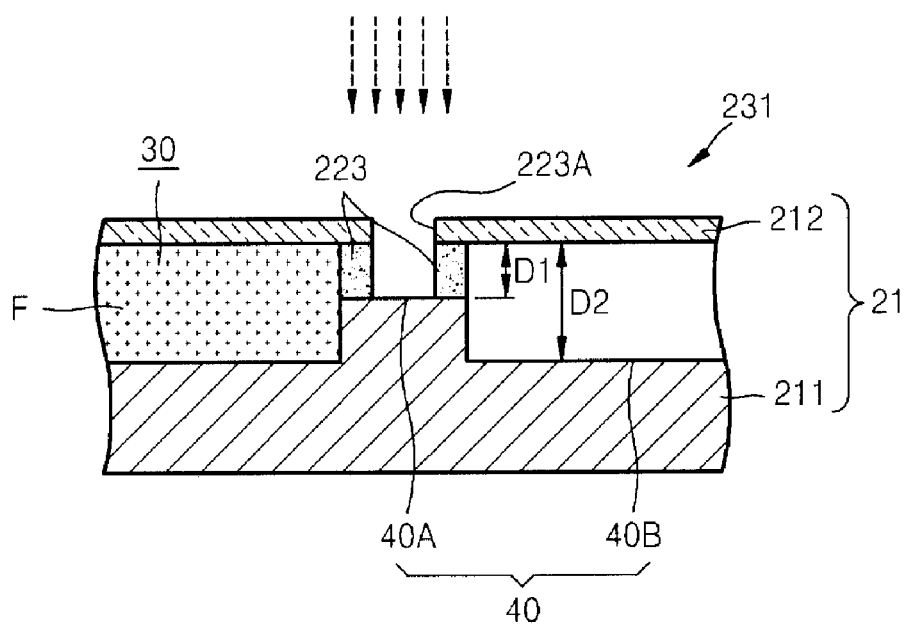
FIG. 6 is a cross-sectional view of phase transition type normally closed valve along a line IV-IV' of FIG. 4.

FIG. 5 is a plan view of the phase transition type normally closed valve 231 that is used in the microfluidic device of FIG. 4. FIG. 6 is a cross-sectional view of the phase transition type normally closed valve 231 taken along line VI-VI' of FIG. 4.

The phase transition type normally closed valve 231 is an outlet valve of the sample chamber 30 and includes a valve plug 223 formed of a valve material that is in a solid state at an ambient temperature. The valve material may be a material in which heating particles are dispersed in a phase transition material that is in a solid state at an ambient temperature. The distribution channel 40 comprises a first area 40A of a first dimension D1 and a second area 40B adjacent to the first area 40A. The second area 40B is of a second dimension D2 larger than D1 and the first area 40A is located at an entrance of the distribution channel 40.

The valve plug 223 completely blocks without a gap a predetermined portion of the first area 40A which is not overlapped with an opening 223A at an ambient temperature. The valve plug 223 is melted at a high temperature and is moved from the first area 40A to the second area 40B, and then the valve plug 223 is again solidified while flow paths of a fluid F is opened. Some of the valve plug 223 may be moved from the first area 40A to the sample chamber 30 after it is melted. The opening 223A functions as an injection inlet that can define a valve plug 223 by injecting a valve material melted when manufacturing the microfluidic device. The valve material injected into the first area 40A through the opening 223A remains in the predetermined portion of the first area 40A by capillary action.

To heat the valve plug 223, an external energy source (see 130L in FIGS. 9 and 130P in FIG. 10) is disposed outside of the microfluidic device, and the external energy source 130L irradiates electromagnetic waves to the initial location of the valve plug 223, that is, to a region including the opening 223A and a circumference thereof. For example, the external energy source 130L may be a laser light source emitting a laser beam. The external energy source 130L may include at least one laser diode. When the laser light source emits a pulse laser beam, the pulse laser beam can have an energy of 1 mJ/pulse or more. When the laser light source emits a continuous wave laser beam, the continuous wave laser beam can have an output of 10 mW or more.

Although a laser light source emitting a laser beam having a wavelength of 808 nm is used in an experiment by the inventors, the present invention is not limited to the laser beam having this wavelength. That is, any laser light source can be used as the external energy source 130L of the microfluidic system so as to emit a laser beam having a wavelength in the range of 400 to 1300 nm.

The sample chamber 30 and the distribution channel 40 can be defined by stereographic patterns that are formed on an inner surface of an upper plate 212 or lower plate 211 which constitutes a disk type platform 21. The upper plate 212 may be formed of an optically transparent material so that electromagnetic waves emitted from an external energy source may be incident to the valve plug 223, and a flow of the fluid F can be observed from the outside. For example, a glass material or a transparent plastic material is advantageous in that the glass material or a transparent plastic material has good optical transparency and manufacturing costs thereof are low.

Heating particles dispersed in the valve plug 223 may have a diameter in the range of 1 nm to 100 μm so as to freely flow in the channel 40 having a width of several thousands of micrometers (μm). The heating particles are characterized in that the temperature of the heating particles is remarkably increased when a laser is irradiated to the heating particles, and as such the heating particles emit heat. In addition, the heating particles are characterized in that they are regularly dispersed in wax. The heating particles may have a structure including a core having a metal component and a shell which is water-repellant so as to have the above properties. For example, the heating particles may have a structure including a core formed of Fe, which is a ferromagnetic material, and a shell formed of a plurality of surfactants coupled to the core and surrounding the core. Generally, the heating particles are stored to be dispersed in carrier oil. The carrier oil may be water-repellant so that the heating particles having a water-repellant surface structure may be regularly dispersed. By filling wax with the carrier oil in which the heating particles are dispersed and mixing the resulting materials, a material used for forming the valve plug 223 may be manufactured. The particle shape of each of the heating particles is not limited to the above examples. That is, each of the heating particles may be a polymer bead, quantum dots, Au nanoparticles, Ag nanoparticles, beads with metal composition, carbon particles or magnetic beads. The carbon particles may include graphite particles.

A phase transition material constituting the valve plug 223 may be wax. Energy of electromagnetic waves, which is absorbed by the heating particles, is transferred to the circumstance in the type of thermal energy, and as such the wax is melted and becomes fluid. Accordingly, the valve plug 223 collapses and the fluid path of fluid F is opened. The wax constituting the valve plug 223 may have an appropriate melting point. If the melting point of the wax is very high, since a long time is required from the time when a laser beam is not emitted to the wax until the time when the wax is melted, it is difficult to minutely control an opening time. On the other hand, if the melting point of the wax is very low, since the wax may partially melt even when a laser beam is not emitted, the fluid F may leak. The wax may be, for example, paraffin wax, microcrystalline wax, synthetic wax, natural wax or the like.

The phase transition material may be gel or a thermoplastic resin. The gel may be polyacrylamide, polyacrylates, polymethacrylates, polyvinylamides or the like. In addition, the thermoplastic resin may be cyclic olefin copolymer (COC), polymethylmethacrylate (acrylic) (PMMA), polycarbonate (PC), polystyrene (PS), polyacetal engineering polymers (POM), perfluoroalkoxy (PFA), polyvinyl chloride (PVC), polypropylene (PP), polyethylene terephthalate (PET), polyetheretherketone (PEEK), polyamide (PA), polysulfone (PSU), polyvinylidene difluoride (PVDF), or the like.

The response time, from the time when a laser beams is emitted to a valve plug of the phase transition type normally closed valve of FIG. 5 until the time when the valve plug is melted to open a channel, is 0.012 seconds.

Figure 7:
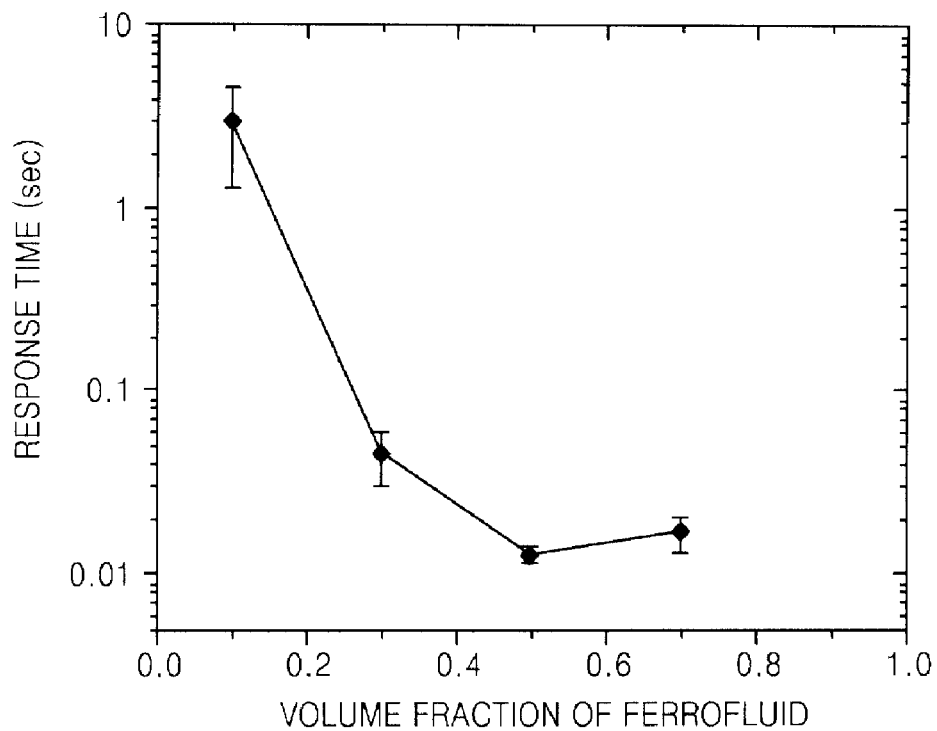
FIG. 7 is a graph illustrating the relationship between the volume fraction of ferrofluid included in the valve plug and the response time with respect to the phase transition type normally closed valve of FIG. 5.

FIG. 7 is a graph illustrating the relationship between the volume fraction of the ferrofluid (dispersion solution of heating particles) included in the valve plug and the response time with respect to the phase transition type normally closed valve of FIG. 5. Magnetic beads may be used in the phase transition type normally closed valve and a phase transition as the heating particles. Usually, the magnetic beads are provided in a type of suspension dispersed in an oil medium. Such suspension is called a magnetic fluid. The valve material described above can be made by mixing a phase transition material (e.g., paraffin wax) and the magnetic fluid. As the volume fraction of the ferrofluid is increased, the response time is roughly reduced. However, irrespective of this, when the volume fraction of the ferrofluid is increased to 70% or more, the maximum hold-up pressure of the valve plug has a tendency to be reduced. Accordingly, the volume fraction of the ferrofluid to be included in the valve plug of the valve unit may be determined according to regulation between the requirement for the response time and the requirement for the maximum hold-up pressure.

Figure 8:
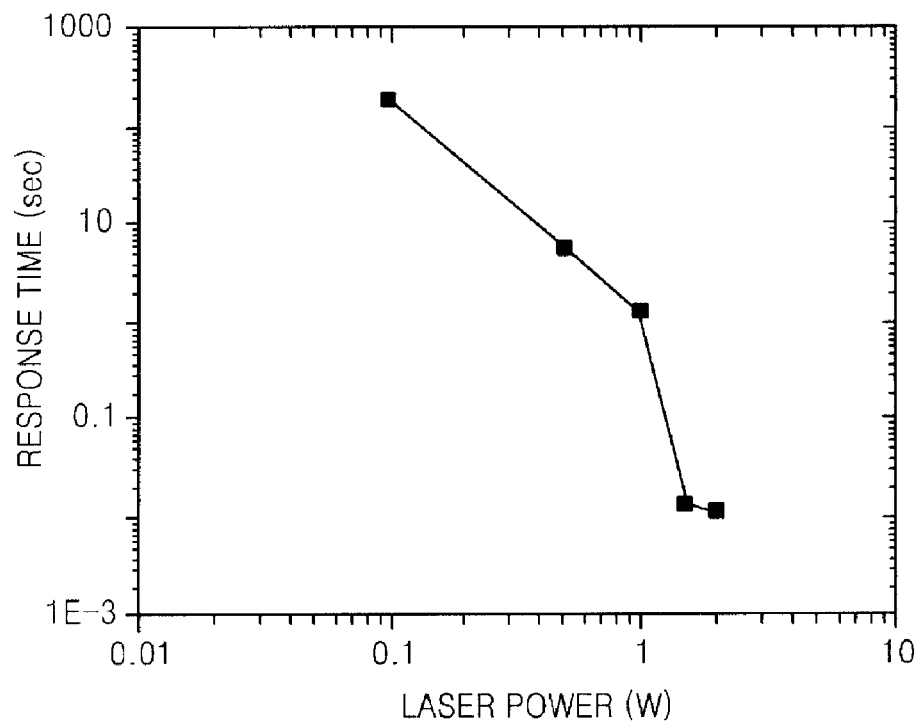
FIG. 8 is a graph illustrating the relationship between the power of a laser light source used as an external energy source and the response time of the normally closed valve with respect to the normally closed valve of FIG. 5.

FIG. 8 is a graph illustrating the relationship between the power of a laser light source used as an external energy source and the response time of the normally closed valve with respect to the normally closed valve of FIG. 5. As the power is increased, the response time is roughly reduced. However, when the power of the laser light source is close to 1.5 W, the response time is slowly changed. Although not illustrated, when the power of the laser light source is greater than 1.5 W, the response time converges to a predetermined minimum response time because there is a limit of the thermal conductivity of paraffin wax. A laser light source having power of 1.5 W is used because of this reason, but the present invention is not limited thereto.

Figure 9:
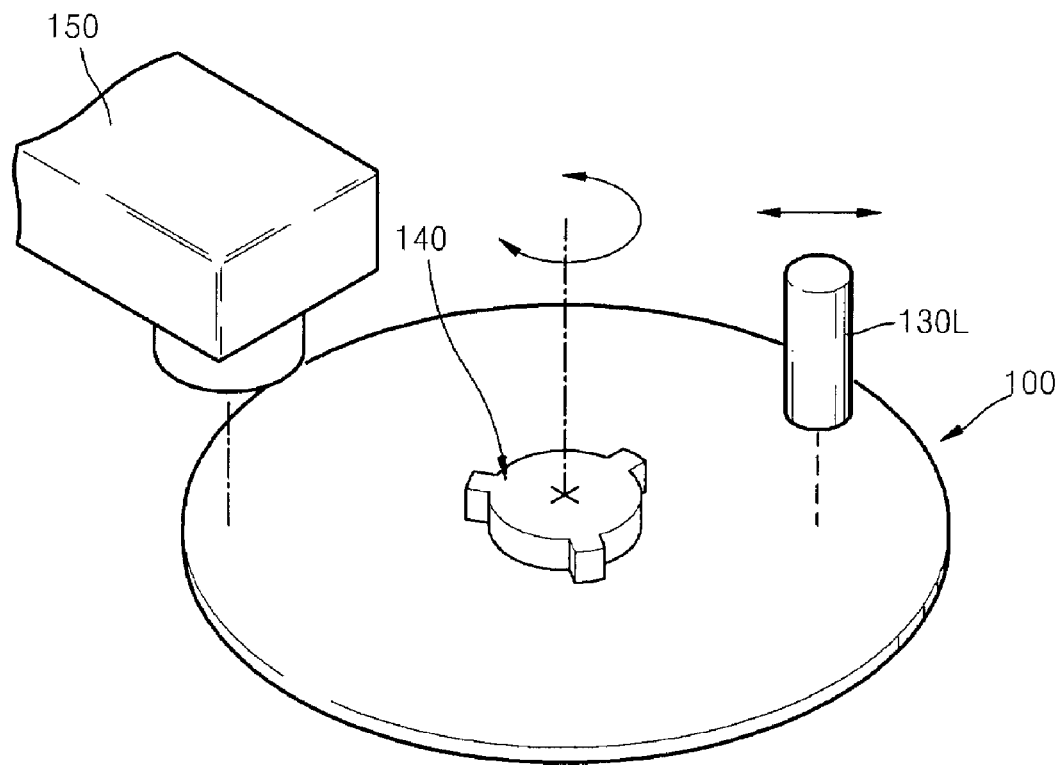
FIG. 9 is a perspective view of a microfluidic system including one of the microfluidic devices of FIGS. 1 and 4, according to an exemplary embodiment of the present invention.

FIG. 9 is a perspective view of a centrifugal microfluidic system including one of the centrifugal microfluidic devices of FIGS. 1 and 4, according to an exemplary embodiment of the present invention. Referring to FIG. 9, the centrifugal microfluidic system according to the current exemplary embodiment of the present invention includes the centrifugal microfluidic device 100 described above. Here, the centrifugal microfluidic system including the centrifugal microfluidic device 100 of FIG. 4 is illustrated as an example. The centrifugal microfluidic system includes an external energy source 130L emitting predetermined electromagnetic waves to supply energy to the phase transition valve 231, which is independently driven as described above. The external energy source 130L may be a device which can emit electromagnetic waves having a predetermined wavelength band, such as microwaves, infrared rays, visible rays, ultraviolet rays or X-rays, preferably, a device which can intensively emit the electromagnetic waves to a short-distance target. The wavelength of waves generated by the external energy source 130L may be in a range such that the waves may be not well absorbed by the heating particles M included in the valve material V. Accordingly, a device generating electromagnetic waves from the external energy source 130L may be appropriately selected according to the materials and surface conditions of the heating particles M. The external energy source 130L may be, for example, a laser light source emitting a laser beam. The laser light source may include at least one laser diode. Details such as the wavelength and the power of the laser beam may be determined according to the kinds of the heating particles included in the phase transition valve of the microfluidic device 100 which is mainly used objective.

The centrifugal microfluidic system according to the current exemplary embodiment of the present invention includes an external energy source controller (not shown) such that electromagnetic waves emitted from the external energy source 130L may be intensively incident on a desired region of the microfluidic device 100, more particularly, a region corresponding to any one of a plurality of phase transition valves included in the microfluidic device 100 by controlling the location and the direction of the external energy source 130L.

In the centrifugal microfluidic system according to the current exemplary embodiment of the present invention, the external energy source controller can move the external energy source 130L facing the platform 21 of the microfluidic device 100 in an arrow direction indicated with respect to the microfluidic device 100, that is, a radial direction of the platform 21. The external energy source 130L may be moved in a straight direction using different mechanisms. These mechanisms are obvious to one of ordinary skill in the art, and thus descriptions thereof will not be included.

The centrifugal microfluidic system according to the current exemplary embodiment of the present invention includes a revolution driving unit 140 driving the platform 21. The revolution driving unit 140 stabilizes the platform 21, and is an element for transmitting rotary power. Although not illustrated, the revolution driving unit 140 may include a motor and a related component thereof, which can revolve the platform 21 by a desired velocity or angular rotation. Similarly to the external energy source controller, a specific example of a structure of the revolution driving unit 140 will not be included. In the microfluidic system according to the current exemplary embodiment of the present invention, the external energy source 130L can intensively emit electromagnetic waves to a selected region of the microfluidic device 100 by help of the external energy source controller and the revolution driving unit 140.

The centrifugal microfluidic system according to the current exemplary embodiment of the present invention may further include a light detector 150 to optically observe various experiments using the diluted sample in the microfluidic device 100. For example, the light detector 150 can detect optical information such as a fluorescent expression or change of optical density of the reaction chamber 50.

Figure 10:
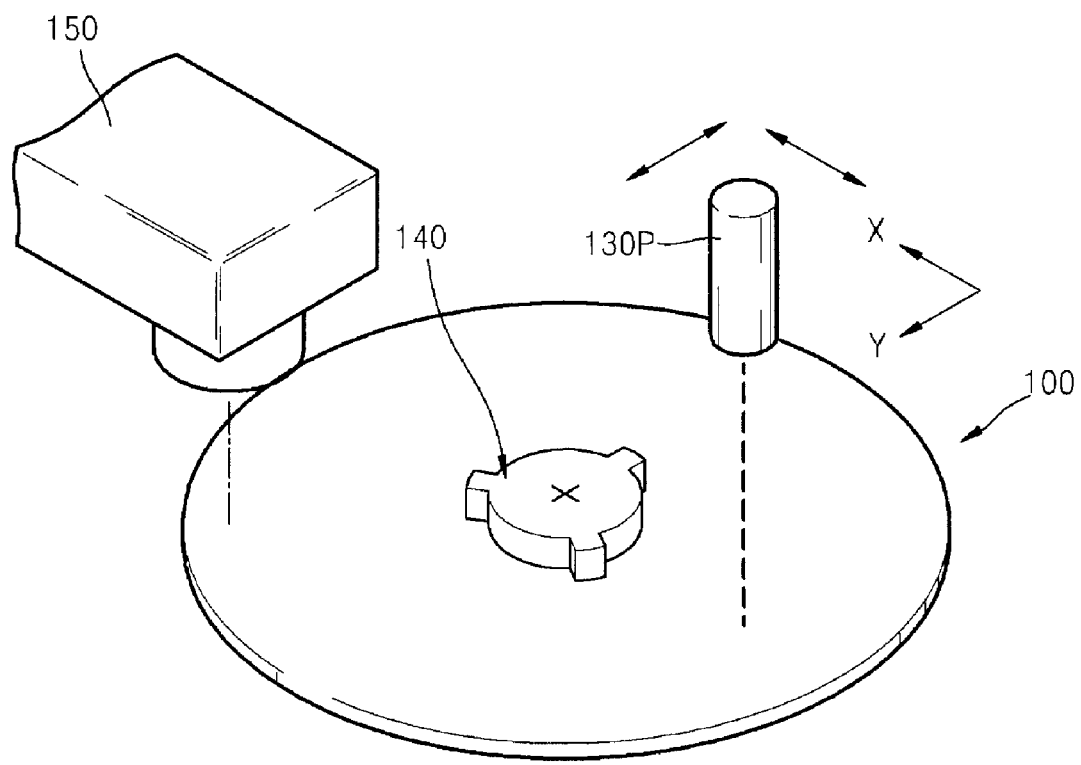
FIG. 10 is a perspective view of a centrifugal microfluidic system including one of the centrifugal microfluidic devices of FIGS. 1 and 4, according to another exemplary embodiment of the present invention.

FIG. 10 is a perspective view of a centrifugal microfluidic system including one of the centrifugal microfluidic devices of FIGS. 1 and 4, according to another exemplary embodiment of the present invention. In the microfluidic system according to the present invention, the descriptions of the centrifugal microfluidic device 100m, the rotation driving unit 140 and the external energy source 130P are the same as those of FIG. 9. However, in the centrifugal microfluidic system according to the current exemplary embodiment of the present invention, an external energy source controller (not shown) may include a plane moving unit such that the external energy source 130P facing the platform 21 may be moved in two directions perpendicular to each other (for example, directions of x and y axes) on a plane parallel to the platform 21, and electromagnetic waves may be emitted to an objective target on the platform 21.

Although not illustrated, the external energy source controller may be configured such that the emitted electromagnetic waves may reach an objective target by changing the direction of the eternal energy source of which location is fixed at a predetermined point over the platform 21.

According to the exemplary embodiments of the present invention, the centrifugal microfluidic device having the sample distribution structure can distribute a sample to a plurality of reaction chambers by one moving operation of a fluid sample. Further, when additional resistances are not added to a moving path of the fluid sample, the sample distribution function can be performed in the microfluidic device, and thus the time of the sample distribution can be reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A centrifugal microfluidic device comprising:
   a rotatable platform;
   a sample chamber which is disposed in the rotatable platform and houses a fluid sample;
   a distribution channel connected to an outlet of the sample chamber;
   a plurality of non-vented reaction chambers which are disposed in the rotatable platform outside of the distribution channel in the radial direction; and
   a plurality of inlet channels which connect the distribution channel with the reaction chambers;
   wherein the fluid sample housed in the sample chamber is distributed to the plurality of non-vented reaction chambers through the distribution channel by a centrifugal force due to a rotation of the rotatable platform, and
   wherein the distribution channel comprises:
   a first section which is connected to an outlet of the sample chamber and extends in a radial direction of the rotatable platform, and
   a second section which extends from the first section in a circumferential direction of the rotatable platform, and wherein a cross section of the distribution channel is substantially the same throughout the first and second sections such that a fluid resistance is substantially the same throughout the first and second sections.

2. The centrifugal microfluidic device of claim 1, wherein a cross section of the distribution channel is constant.

3. The centrifugal microfluidic device of claim 1, wherein each of the plurality of inlet channels comprises a barrier rib branching an inner part of the inlet channels into first and second sub channels.

4. The centrifugal microfluidic device of claim 3, wherein an inside of the barrier rib clogs a part of the distribution channel so that a fluid resistance generated when the fluid sample proceeds along the distribution channel is less than or equal to a fluid resistance generated when the fluid sample proceeds towards the sub channel.

5. The centrifugal microfluidic device of claim 1, wherein the distribution channel comprises a plurality of guide protrusions that guide a fluid sample flowing along the distribution channel and are formed at portions where the inlet channel is connected to the distribution channel.

6. The centrifugal microfluidic device of claim 5, wherein each of the guide protrusions protrudes towards a corresponding inlet channel at an intersection between an inner wall of the distribution channel and a central line that extends to equally divide a width of the corresponding inlet channel.

7. The centrifugal microfluidic device of claim 1, wherein a fluid resistance at inlet channels is greater than a fluid resistance at the distribution channel.

8. The centrifugal microfluidic device of claim 7, wherein the distribution channel comprises a consecutive wave section which has a triangular wave shape structure and is connected to the non-vented reaction chambers via the inlet channels.

9. The centrifugal microfluidic device of claim 8, wherein a fluid resistance at each of the inlet channels is greater than a fluid resistance at the distribution channel.

10. The centrifugal microfluidic device of claim 1, further comprising a valve which is disposed in the outlet of the sample chamber.

11. The centrifugal microfluidic device of claim 10, wherein the valve comprises a phase transition type normally closed valve which contactlessly driven by an external energy source.

12. A centrifugal microfluidic system comprising:
    a centrifugal microfluidic device;
    a rotation driving unit rotating so as to support the centrifugal microfluidic device and control the centrifugal microfluidic device; and
    a valve driving unit,
    wherein the centrifugal microfluidic device comprises:
    a rotatable platform;
    a sample chamber which is disposed in the rotatable platform and houses a fluid sample;
    a distribution channel connected to an outlet of the sample chamber;
    a plurality of non-vented reaction chambers which are disposed in the rotatable platform outside of the distribution channel in the radial direction;
    a plurality of inlet channels which connect the distribution channel with the reaction chambers; and
    a valve which is disposed in the outlet of the sample chamber and is driven by the valve driving unit,
    wherein the fluid sample housed in the sample chamber is distributed to the plurality of non-vented reaction chambers through the distribution channel by a centrifugal force due to a rotation of the rotatable platform, and
    wherein the distribution channel comprises:
    a first section which is connected to an outlet of the sample chamber and extends in a radial direction of the rotatable platform, and
    a second section which extends from the first section in a circumferential direction of the rotatable platform, and wherein a cross section of the distribution channel is substantially the same throughout the first and second sections such that a fluid resistance is substantially the same throughout the first and second sections.

13. The centrifugal microfluidic system of claim 12, wherein the valve driving unit comprises:
    an external energy source which emits an electromagnetic wave that heats the valve; and
    an external energy source controller which controls a location and a direction of the external energy source so that the electromagnetic wave emitted by the external energy source is intensively incident on a region corresponding to the valve.

14. The centrifugal microfluidic system of claim 13, wherein the external energy source controller comprises a straight moving unit which moves the external energy source facing a platform of the microfluidic device in the radial direction of the rotatable platform.

15. The centrifugal microfluidic system of claim 13, wherein the external energy source supplier comprises a plane moving unit which moves the external energy source facing the platform of the microfluidic device in two directions on a plane parallel to the rotatable platform with respect to rectangular coordinates.

16. The centrifugal microfluidic system of claim 12, further comprising a light detector that optically detects a reaction result of each of the reaction chambers of the centrifugal microfluidic device.

17. The centrifugal microfluidic system of claim 12, wherein each of the inlet channels comprises a barrier rib branching an inner part of the inlet channel into two sub channels.

18. The centrifugal microfluidic system of claim 12, wherein the distribution channel comprises a plurality of guide protrusions that guide a fluid sample flowing along the distribution channel and are formed at portions where the inlet channel is connected to the distribution channel.

19. The centrifugal microfluidic system of claim 12, wherein the distribution channel comprises a consecutive wave section which has a triangular wave shape structure and is connected to the non-vented reaction chambers via the inlet channels.

20. The centrifugal microfluidic system of claim 12, wherein the distribution channel comprises a first section which is connected to an outlet of the sample chamber and extends in a radial direction of the rotatable platform, and a second section which extends from the first section in a circumferential direction of the rotatable platform, and wherein a fluid resistance is the same throughout the first and second sections.

21. A centrifugal microfluidic device comprising:
a rotatable platform;
a sample chamber which is disposed in the platform and houses a fluid sample;
a distribution channel which is connected to an outlet of the sample chamber;
a plurality of non-vented reaction chambers which are disposed in the rotatable platform outside of the distribution channel in the radial direction; and
a plurality of inlet channels which connect the distribution channel with the reaction chambers;
a valve which is disposed in the outlet of the sample chamber and comprises a material which causes the valve to open when heated;
wherein the fluid sample housed in the sample chamber is distributed to the plurality of non-vented reaction chambers through the distribution channel by a centrifugal force due to a rotation of the rotatable platform when the valve is heated, and
wherein the distribution channel comprises:
a first section which is connected to an outlet of the sample chamber and extends in a radial direction of the rotatable platform, and
a second section which extends from the first section in a circumferential direction of the rotatable platform, and wherein a cross section of the distribution channel is substantially the same throughout the first and second sections such that a fluid resistance is substantially the same throughout the first and second sections.

22. The centrifugal microfluidic device of claim 21, wherein the valve is a phase transition type normally closed valve comprising a phase transition material in which heating particles are dispersed.

23. The centrifugal microfluidic device of claim 21, wherein the valve comprises a valve plug formed of a material that is in a solid state at an ambient temperature, the distribution channel comprises a first area of a first dimension located at an entrance of the distribution channel and a second area of a second dimension adjacent to the first area, and when the valve plug is melted by the external energy source, the valve plug is moved from the first area to the second area so that the fluid sample flows from the sample chamber through the distribution channel.

24. The centrifugal microfluidic device of claim 1, wherein the fluid sample and air in the non-vented reaction chamber displaced by the fluid sample must pass through the same plurality of inlet channels.

25. The centrifugal microfluidic device of claim 1, wherein each non-vented reaction chamber has only one inlet channel from among the plurality of inlet channels, and each of the plurality of inlet channels is connected to the distribution channel.

26. The centrifugal microfluidic device of claim 1, wherein each of the plurality of inlet channels connect directly to each of the plurality of non-vented reaction chambers.

27. The centrifugal microfluidic device of claim 21, wherein each of the plurality of inlet channels comprises a barrier rib branching an inner part of the inlet channel into two sub channels.

28. The centrifugal microfluidic device of claim 1, wherein each of the plurality of inlet channels includes a first sub channel through which the fluid sample flows into a corresponding non-vented reaction chamber and second sub channel through which air in the corresponding non-vented reaction chamber is exhausted.

29. The centrifugal microfluidic device of claim 21, wherein each of the plurality of inlet channels includes a first sub channel through which the fluid sample flows into a corresponding non-vented reaction chamber and second sub channel through which air in the corresponding non-vented reaction chamber is exhausted.

* * * * *